US009415390B2

(12) United States Patent
Gumbrecht et al.

(10) Patent No.: US 9,415,390 B2
(45) Date of Patent: Aug. 16, 2016

(54) FLAT BODY IN MANNER OF CHIP CARD FOR BIOCHEMICAL ANALYSIS AND METHOD OF USING

(75) Inventors: Walter Gumbrecht, Herzogenaurach (DE); Peter Paulicka, Röttenbach (DE); Jörn Ueberfeld, Sterrebeek (BE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 920 days.

(21) Appl. No.: 13/498,871

(22) PCT Filed: Sep. 27, 2010

(86) PCT No.: PCT/EP2010/064258

§ 371 (c)(1),
(2), (4) Date: Mar. 28, 2012

(87) PCT Pub. No.: WO2011/036289

PCT Pub. Date: Mar. 31, 2011

(65) Prior Publication Data

US 2012/0184043 A1 Jul. 19, 2012

(30) Foreign Application Priority Data

Sep. 28, 2009 (DE) ........................ 10 2009 043 226

(51) Int. Cl.
*G01N 33/50* (2006.01)
*G01N 33/68* (2006.01)
(Continued)

(52) U.S. Cl.
CPC ........... *B01L 3/502715* (2013.01); *B01L 3/021* (2013.01); *B01L 3/5082* (2013.01); (Continued)

(58) Field of Classification Search
CPC . B01L 3/502715; B01L 3/021; B01L 3/5082; B01L 2300/0883; B01L 2300/0887; B01L 2300/0672; B01L 2300/0816; B01L 2300/0663; B01L 2400/0406; B01L 2200/027; Y10T 436/143333; G01N 2001/002; G01N 1/10; G01N 1/14; G01N 1/1418; G01N 1/1427; G01N 1/1436; G01N 1/1445; G01N 1/1454; G01N 1/1463; G01N 1/1472; G01N 27/26; G01N 33/50
See application file for complete search history.

(56) References Cited

U.S. PATENT DOCUMENTS

| | | | |
|---|---|---|---|
| 5,747,666 | A | 5/1998 | Willis |
| 5,804,437 | A | 9/1998 | Tegeler et al. |

(Continued)

FOREIGN PATENT DOCUMENTS

| | | | |
|---|---|---|---|
| CN | 1254845 | A | 5/2000 |
| DE | 199 64 337 | B4 | 9/2004 |

(Continued)

OTHER PUBLICATIONS

International Search Report for PCT/EP2010/064258; mailed Dec. 27, 2010.

(Continued)

*Primary Examiner* — Christopher A Hixson
(74) *Attorney, Agent, or Firm* — David S. Safran

(57) ABSTRACT

At least two microfluidic devices and at least one sensor chip are formed in a flat body. The at least one sensor chip is in direct contact with at least one first microfluidic device. A second microfluidic device in the manner of a pipette is integral with the flat body or connected thereto. The flat body may be used by docking an E-cup by way of a clamping device of the flat body to the flat body and exchanging fluid between the E-cup and the flat body by way of the second microfluidic device.

13 Claims, 2 Drawing Sheets

(51) Int. Cl.
*B01L 3/00* (2006.01)
*B01L 3/02* (2006.01)

(52) U.S. Cl.
CPC .... *B01L2200/027* (2013.01); *B01L 2300/0663* (2013.01); *B01L 2300/0672* (2013.01); *B01L 2300/0816* (2013.01); *B01L 2300/0883* (2013.01); *B01L 2300/0887* (2013.01); *B01L 2400/0406* (2013.01); *Y10T 436/143333* (2015.01)

(56) References Cited

U.S. PATENT DOCUMENTS

| | | | |
|---|---|---|---|
| 6,602,472 | B1 | 8/2003 | Zimmermann et al. |
| 2002/0009392 | A1 | 1/2002 | Wolk et al. |
| 2003/0104634 | A1 * | 6/2003 | Jacobs et al. .................. 436/180 |
| 2005/0031490 | A1 | 2/2005 | Gumbrecht et al. |
| 2005/0130292 | A1 | 6/2005 | Ahn et al. |
| 2006/0165558 | A1 | 7/2006 | Witty et al. |
| 2006/0228259 | A1 | 10/2006 | Samsoondar |
| 2007/0172388 | A1 | 7/2007 | Padmanabhan et al. |
| 2008/0172025 | A1 | 7/2008 | Tanaami et al. |
| 2009/0140170 | A1 | 6/2009 | Nevill et al. |
| 2009/0186344 | A1 | 7/2009 | Farinas |
| 2009/0205447 | A1 | 8/2009 | Sugimoto et al. |
| 2009/0215125 | A1 | 8/2009 | Reed et al. |
| 2011/0059547 | A1 | 3/2011 | Dehal et al. |

FOREIGN PATENT DOCUMENTS

| | | | |
|---|---|---|---|
| DE | 102005049976 | A1 | 4/2006 |
| DE | 102008004646 | A1 | 7/2008 |
| DE | 102009043226.4 | | 9/2009 |
| EP | 0 897 750 | A2 | 2/1999 |
| EP | 0 992 287 | A2 | 4/2000 |
| EP | 2 037 280 | A1 | 3/2009 |
| JP | 2004-500578 | | 1/2004 |
| JP | 2004-532396 | | 10/2004 |
| JP | 2008-524605 | | 7/2008 |
| WO | 2006/069328 | A2 | 6/2006 |
| WO | WO2008002483 | A2 * | 1/2008 |
| WO | 2009/115608 | A2 | 9/2009 |

OTHER PUBLICATIONS

Office Action mailed Jan. 3, 2014 in corresponding Chinese Application No. 201080043136.0.

* cited by examiner

FLAT BODY IN MANNER OF CHIP CARD FOR BIOCHEMICAL ANALYSIS AND METHOD OF USING

CROSS REFERENCE TO RELATED APPLICATIONS

This application is the U.S. national stage of International Application No. PCT/EP2010/064258, filed Sep. 27, 2010 and claims the benefit thereof. The International Application claims the benefits of German Application No. 10 2009 043 226.4 filed on Sep. 28, 2009, both applications are incorporated by reference herein in their entirety.

BACKGROUND

Described below is a flat body in the manner of a chip card for biochemical analysis of substances and a method for the use thereof. The flat body has at least two microfluidic devices and at least one sensor chip. The at least one sensor chip is integrated in the flat body and is in direct contact with at least one first microfluidic device.

Lab-on-a-chip systems are used in biosensory applications in order to be able to carry out biochemical analyses in a simple and cost-effective manner. Thus, for example, DE 10 2005 049 976 A1 has disclosed a flat body for biochemical analysis of substances such as e.g. DNA and proteins. This flat body has the shape of a chip card, which has an analogous design to a credit card. The flat body includes a semiconductor chip with a sensor array and integrated circuits, the semiconductor chip being cast in a flat material made of plastic and electrically connected to electric contacts for reading out the chip by an external readout unit. Microfluidic devices such as e.g. reaction chambers and channels are formed on a front side of the flat body as depressions in the material made of plastic. A film is adhesively bonded onto the front side and the microfluidic devices are thus sealed in a fluid-tight manner, i.e. sealed with respect to liquids and/or gasses, against the surroundings.

During a biochemical analysis of a liquid as provided by e.g. blood or urine, the film of the chip card is pierced by a sharp needle analogous to a syringe tip, and the liquid is injected into a microfluidic device of the chip card. The liquid comes into contact with sensors of the sensor array on the chip via channels and reaction chambers and components of the liquid can be detected directly or indirectly. Detection can take place by optical or electrochemical detectors. Substances that are necessary for chemical reactions for detecting the components of the liquid can already be situated on or in the chip card, or can likewise be injected into the latter by a sharp needle.

The intake capacity of microfluidic devices on a chip card for holding liquid is generally only very small and is often restricted to only a few milliliters or to microliters or, in an extreme case, only to nanoliters. In the case of biochemical substances that only occur at very low concentrations in the liquid to be examined, this may lead to the overall amount of liquid by which the chip card can be filled not sufficing to reach or exceed the detection limit of the biochemical substance. The biochemical substance can then only be detected if the biochemical substance is chemically multiplied, e.g. by PCR in the case of DNA. In the case of detecting whole cells, a time- and cost-intensive multiplication may become necessary, e.g. in an incubator. In the case of e.g. chemical trace elements in urine or water, chemical multiplication may be excluded, and hence detection may only be possible with great difficulty or not at all.

A further problem in supplying liquid to or into the chip card by sharp needles may lie in the introduction of contaminants. Particularly in view of detecting trace elements, DNA or peptides, very small amounts of chemical or biochemical contaminants may lead to errors in the quantitative and/or qualitative detection. The probability of contamination increases with every additional apparatus, as constituted by e.g. a needle, with which the liquid to be examined is brought into contact. Increased complexity, which is time- and cost-intensive, must be carried out to ensure the detection quality, e.g. by thorough cleaning of all apparatuses.

SUMMARY

Thus, an aspect is to specify a flat body in the manner of a chip card for biochemical analysis and, in particular, a method for the use thereof, by which it becomes possible in a simple and cost effective manner to introduce fluids such as e.g. liquids directly from a vessel into microfluidic devices of the flat body. In particular, it is possible to introduce fluids into the microfluidic devices of the flat body, with the fluids being brought into contact or flowing through as few self-sufficient individual components as possible. Furthermore, described below is a flat body to/from which large amounts of fluid can be directly supplied from and/or discharged into a vessel, as is constituted by e.g. an E-cup.

The flat body in the manner of a chip card for biochemical analysis of substances includes at least two microfluidic devices and at least one sensor chip. The at least one sensor chip is integrated in the flat body and is in direct contact with at least a first microfluidic device. The flat body integrally includes a second microfluidic device in the manner of a pipette. Here integrally means that the second microfluidic device and the remaining flat body are produced together from at least one material and form a contiguous body without the second microfluidic device being plugged or clamped onto the flat body or attached to the latter in any other repeatedly separable and attachable manner.

The advantage of a flat body with an integrated pipette lies in the option of easily and quickly interchanging large amounts of liquid between a vessel, as constituted by e.g. an E-cup, and the flat body. Since the flat body and the pipette integrated therein can be produced together from one material, both have the same chemical and biochemical levels of purity. This prevents the introduction of contaminants into the flat body as a result of additional parts. The possible production in one step reduces costs and complexity and leads to higher stability than in the case of plug-on solutions of e.g. syringes/cannulae/needles made of metal.

The flat body can include a first clamping device, which is designed to attach an E-cup onto the flat body in a direct mechanical manner. E-cups are used as reaction vessels and are, for example, available from Eppendorf® and are then known by the abbreviation “Eppi”. The vessels have various sizes as a standard and can accordingly take up different volumes of solution, e.g. between 0.2 ml and 2 ml. They are distinguished by good resistance to chemicals and are dimensionally stable to over 100° C. The clamping device would have a diameter substantially equal to the internal diameter of an E-cup to be attached at the opening thereof. Mechanical attachment of the E-cup directly to the flat body by clamping constitutes a particularly simple and stable option of attaching the E-cup to the flat body.

The flat body may include a second clamping device, which is designed to attach a cover of an E-cup onto the flat body in a direct mechanical manner. This increases the stability of the attachment of an E-cup on the flat body and leads to an improvement in the handling because the cover does not interfere during filling, or removing the liquid from, the E-cup by being moveable relative to the flat body.

The second microfluidic device may have an elongate design and at one end may include a tip with a fluidic opening. It can be designed such that when an E-cup is attached to the first and/or second clamping device, the tip of the second microfluidic device is arranged with the fluidic opening in the region of a lower end of the E-cup. This enables an almost complete removal of liquid from the E-cup with the aid of the second microfluidic device.

The flat body may be formed of a material made of plastic, more particularly an injection-molded plastic. Injection-molded plastic is easy to process and allows a cost-effective production of the flat body. The microfluidic devices can be formed on a front side of the flat body and can be covered by a film, more particularly a self-adhesive film made of a material made of plastic. This enables a simple and cost-effective production of the flat body with microfluidic devices.

The at least two microfluidic devices can include channels and/or chambers, which are embodied as depressions in a flat plane on the front side of the flat body. Furthermore, the at least two microfluidic devices can include valves, which are formed in the flat body. The at least two microfluidic devices can also include a recess, which is formed as a depression in a flat plane on the rear side of the flat body and in which the sensor chip is embedded, more particularly with electric contacts of the sensor chip in a plane with the flat plane on the rear side of the flat body and/or with a sensor array of the sensor chip in direct contact with at least one chamber on the front side of the flat body. As a result, the at least two microfluidic devices are suitable for enabling good handling of liquids and for transporting liquids from an E-cup to sensors on the chip. There may be chemical reactions of liquids or substances in the liquids in e.g. chambers with solid phase reagents on the path from the E-cup to the sensors.

The flat body can have a thickness in the region of one millimeter, a length in the region of 85 millimeters and a width in the region of 54 millimeters. At least one microfluidic device can be designed to contain dry reagents, particularly in channels and/or reaction chambers with a cross section in the region of one or more square millimeters. The second microfluidic device can have a length in the region of 45 millimeters.

The second microfluidic device can be in fluidic contact with sensors of the sensor chip via the first microfluidic device.

A cross section through the second microfluidic device perpendicular to the front side of the flat body can have a substantially rectangular outer circumference with an open recess toward the front side of the flat body. This achieves increased stability during simple production because the second microfluidic device has the flat shape of the flat body.

The sensor chip can include an array of electrochemical sensors. As a result, the flat body is able to undertake electrochemical measurements, which are simpler, more cost-effective and more readily carried out in a small space than optical measurements. The sensor chip can furthermore include an integrated circuit for processing electric signals from the sensors. The sensor chip can also include electric contacts for electric readout of the sensor chip, more particularly for electric readout of the sensor chip with the aid of an external data processing unit.

The flat body can have at least one opening on its front and/or rear side, which is in fluidic contact with the at least one first microfluidic device and/or which is designed to connect to an exterior pump. Small amounts of substances, particularly in liquid form, used for the detection can additionally be supplied to the flat body via this opening or these openings. Thus, e.g. labeling substances can be supplied to the microfluidic devices of the flat body in fresh form prior to an actual electrochemical measurement of the liquid from an E-cup and can react with substances in the liquid. Negative pressure in the microfluidic devices can also be generated via the at least one opening, e.g. with the aid of a pump, and serve to suction liquid from an E-cup into the flat body or the microfluidic devices thereof.

A method for using the above-described flat body includes the following:

- an E-cup is filled with a liquid to be examined, and
- the second microfluidic device is introduced into the E-cup such that it is in direct contact with the liquid to be examined, and
- the liquid is transported into the first microfluidic device through the second microfluidic device, in particular directly and in particular by negative pressure and/or capillary forces, and
- the liquid to be examined is routed over the sensor chip, and
- at least one sensor of the sensor chip interacts with at least one chemical and/or biochemical substance of the liquid to be examined and/or with a reaction product of a substance of the liquid to be examined.

Here, the second microfluidic device can take up liquid from the E-cup in a first step and emit liquid into the E-cup in a second step, with, in particular, the first and the second step being repeated in an interval-like manner. This affords the possibility of a type of rinsing of the microfluidic devices with liquid from the E-cup. Furthermore, it is possible to carry out reactions that require a large amount of solution with a large volume not in the microfluidic devices but in a docked E-cup. A combination of reactions in the E-cup and the microfluidic devices in a different sequence is likewise possible in this manner.

By way of example, blood, urine, fresh water or waste water can be used as liquid to be examined. The flat body and the method for the use thereof are particularly well suited, but not restricted, to use in the case of low concentrations of the substance to be detected and large solution volumes of the liquid required for the detection. If the concentration of the substance to be detected is so low that a volume of the liquid required for the detection exceeds the capacity of the microfluidic devices formed in or on the flat body, reactions can be carried out in a docked E-cup and the liquids that have finished their reactions can be supplied to the sensors of the sensor chip in the flat body via the second microfluidic device. The sensors of the sensor chip can detect e.g. DNA, RNA, peptides or antibodies. Substances involved in the detection and preparation, e.g. by lysis of cells, can be stored, in particular as dry reagents, in e.g. chambers or channels of the flat body. For the chemical reaction, liquid can be suctioned into the microfluidic devices from an E-cup and mixed with the stored substances, e.g. for dissolving dry reagents, and it can subsequently be returned to the E-cup. A larger liquid volume can then react in the E-cup than in the microfluidic devices. Subsequently, part of the liquid in the E-cup can be drawn into the second microfluidic device via the first, e.g. by an applied negative pressure at openings of the first microfluidic device, and at the sensors there may be a detection of reaction products or substances directly contained in the liquid.

The advantages connected to the method for using a flat body are analogous to the advantages that were described above in respect of the flat body.

BRIEF DESCRIPTION OF THE DRAWINGS

These and other aspects and advantages will become more apparent and more readily appreciated from the following description of the exemplary embodiments, taken in conjunction with the accompanying drawings of which.

DETAILED DESCRIPTION OF THE PREFERRED EMBODIMENT

Figure 1:
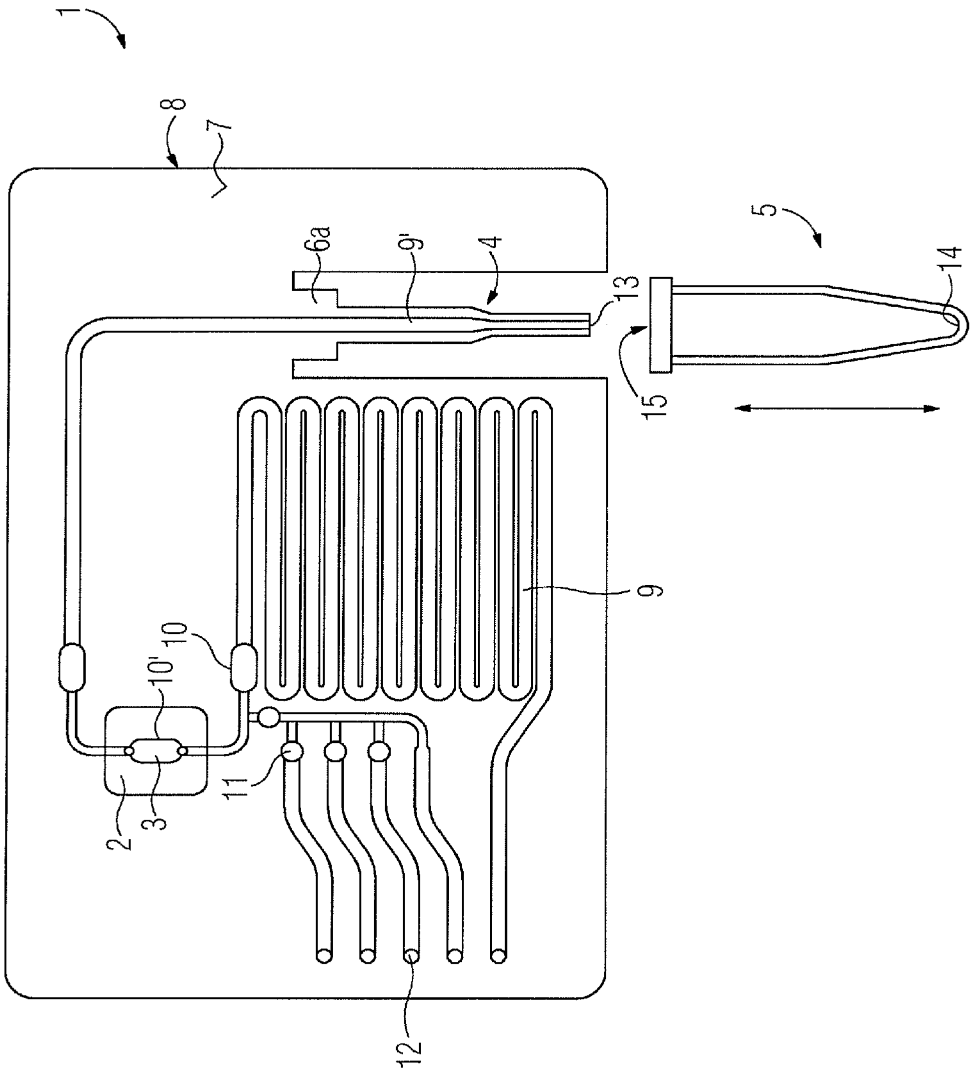
FIG. 1 is a schematic plan view on a front side of the flat body with a first and a second microfluidic device in the manner of a pipette and with a clamping device for an E-cup.

Reference will now be made in detail to the preferred embodiments, examples of which are illustrated in the accompanying drawings, wherein like reference numerals refer to like elements throughout.

FIG. 1 illustrates a plan view on a front side 7 of the flat body 1 without a cover and a section through an E-cup 5. The flat body 1 is embodied in the form of a chip card or in the form of a credit card. Values for the dimensions of such a chip card are e.g. height H×width B×depth D equaling 5.5 cm×8.5 cm×0.1 cm. Microfluidic devices 4, 7 are embodied on the front side 7 as depressions in the flat body 1. By way of example, the flat body 1 may be formed of a material made of plastic, more particularly an injection-molded plastic. By way of example, microfluidic devices 4 are channels 9 and chambers 10, which can have a width in the region of 1 mm to 5 mm and a depth of approximately 100 μm. By way of example, chambers can have a length of between 1 mm and 10 mm and channels can have a length in the region of 1 cm up to 100 cm. Reagents, e.g. in dried form, may be stored in the microfluidic devices 4.

A sensor chip 2 is attached, e.g. by adhesive bonding, in a recess on the rear side 8 of the flat body 1 which can have dimensions of height H'×width B'×depth T' in the region of 1.4 cm×1.3 cm×800 μm. The sensor chip 2 with a sensor array on one side and electric contacts for reading out the sensor chip 2 on the other side of the sensor chip 2 is arranged in the recess such that the side of the sensor chip 2 with the sensor array forms the base of a microfluidic chamber 10' serving as a reaction and/or detection chamber. The side of the sensor chip 2 with the electric contacts forms a plane with the rear side 8 of the flat body 1. Sensors of the sensor array can detect substances or reaction products in a liquid situated in the microfluidic chamber 10' by optical or electrochemical detectors. Electric signals from the sensors can be transmitted to external measurement and data processing devices via the electric contacts of the sensor chip 2 or can be processed by integrated circuits on the sensor chip 2 and be displayed directly or transmitted via the electric contacts.

Liquids that are used for preparing the sample, for e.g. cell lysis and/or for detection reactions, can be supplied to the microfluidic devices 3, 9, 10, 10' via inlet and outlet openings 12 and microfluidic channels 9. The supply can be controlled by valves 11, which are formed in the flat body 1. It is also possible to supply or remove fluids such as air to/from the flat body via the inlet and outlet openings 12, with positive or negative pressure being generated in the microfluidic devices 3, 9, 10, 10'.

Accordingly, the flat body 1 includes a second microfluidic device 4, which has the shape and function of a flattened pipette. The second microfluidic device 4 is produced in one piece together with the flat body, e.g. from plastic. The length L can be in the region of 2.5 cm, depending on the size of an E-cup 5 to be used. The length should almost equal the depth of the E-cup 5, i.e. the distance between the opening 15 and the base 14 of the E-cup 5. This enables almost complete removal of liquid from an E-cup 5 with the aid of the second microfluidic device 4. The thickness of the second microfluidic device 4 equals the thickness of the flat body, e.g. 1 mm. A channel 9' is formed as a depression, centrally in the second microfluidic device 4 on the front side 7 of the flat body 1, the channel 9' approximately corresponding to the dimension of channels 9 of the first microfluidic device 3 in the remainder of the flat body 1. Thus, the width thereof is in the region of 1 mm and the depth thereof is in the region of 100 μm. The channel 9' has a fluidic connection to sensors of the sensor chip 2 via channels 9 and/or chambers 10. The width of the second microfluidic device 4 is e.g. 2 mm.

An E-cup 5 can be attached to the flat body 1 by clamping by a clamping device **6*a* of the flat body 1. FIG. 1 illustrates a section through an E-cup 5. Reaction vessels in the form of "Eppis" can be used as E-cup 5, which e.g. hold a liquid volume in the region of 1 ml to 100 ml. A liquid to be examined such as e.g. blood, urine, tap water or drinking water may be contained in the E-cup 5 as liquid. This liquid can be prepared in the E-cup 5 for an examination. Thus, in the E-cup 5, e.g. cells can be broken down, DNA can be multiplied, markers can be coupled and/or specific molecules can be fished out or increased in concentration via beads. Alternatively, the liquid to be examined can be introduced untreated into the flat body 1 via the second microfluidic device 4. Instead of the liquid to be examined, the E-cup 5** can contain substances involved in an examination as a liquid.

The second microfluidic device 4 has a fluidic connection to the first microfluidic device 3 and is introduced into an E-cup 5 such that, as a result of capillary forces or negative pressure in the first microfluidic device 3, liquid from the E-cup 5 enters the first microfluidic device 3 and reaches the sensor array of the sensor chip 2 via the second microfluidic device 4. As a result of positive pressure in the first microfluidic device 3, liquid can be introduced into the E-cup 5 from the first microfluidic device 3 via the second microfluidic device 4. By way of example, this enables chemical reactions, which require a large solution volume and for this reason cannot be carried out in a microfluidic device 3, to take place "outsourced" in the E-cup. The reaction product can subsequently be processed further in the flat body 1 or be directly detected by the sensors.

For simple handling of an E-cup 5 in conjunction with the flat body 1, the clamping apparatus **6*a* is embodied as a widening of the second microfluidic device 4. This affords a simple and cost-effective production of the clamping device 6*a* together with the flat body 1 including the second microfluidic device 4 in one step as an integral body from injection-molded plastic. The microfluidic devices 3, 4 are sealed with the aid of a film. Thus, for example, a self-adhesive and/or adhesively bonded film can completely cover the front side 7 of the flat body 1, including the first and second microfluidic devices 3, 4. Alternatively, a thermally welded film can be partly or wholly applied to the flat body 1. The openings 12 can be pierced by needles when required. An opening at the tip 13 of the second microfluidic device 4 can likewise be produced when required by being ripped open, cut open or pierced, or the opening at the tip 13 can alternatively be formed when a film is applied to the flat body 1**.

The clamping apparatus **6*a* substantially has a width corresponding to the internal diameter of the opening 15 of the E-cup, or is slightly larger, e.g. by approximately 1 mm. The simplest form of the clamping device is rectangular, in particular with rounded-off corners. When the E-cup 5 is pushed onto the clamping device 6*a*, two opposing edges press against the inner wall of the E-cup in the region of the opening 15. Friction leads to mechanical clamping of the E-cup 5 on the flat body 1, specifically on the clamping device 6***a* of the flat body 1. There is also simple pushing of the E-cup 5 onto the clamping device 6*a* if the clamping device 6*a* has the outline of a section through a barrel, with convex curvatures on the two opposing edges. For reasons of simplicity, FIG. 1 only shows a rectangular form of the clamping device 6*a*. The thickness of the clamping device equals or substantially equals the thickness of the remainder of the flat body 1.

Figure 2:
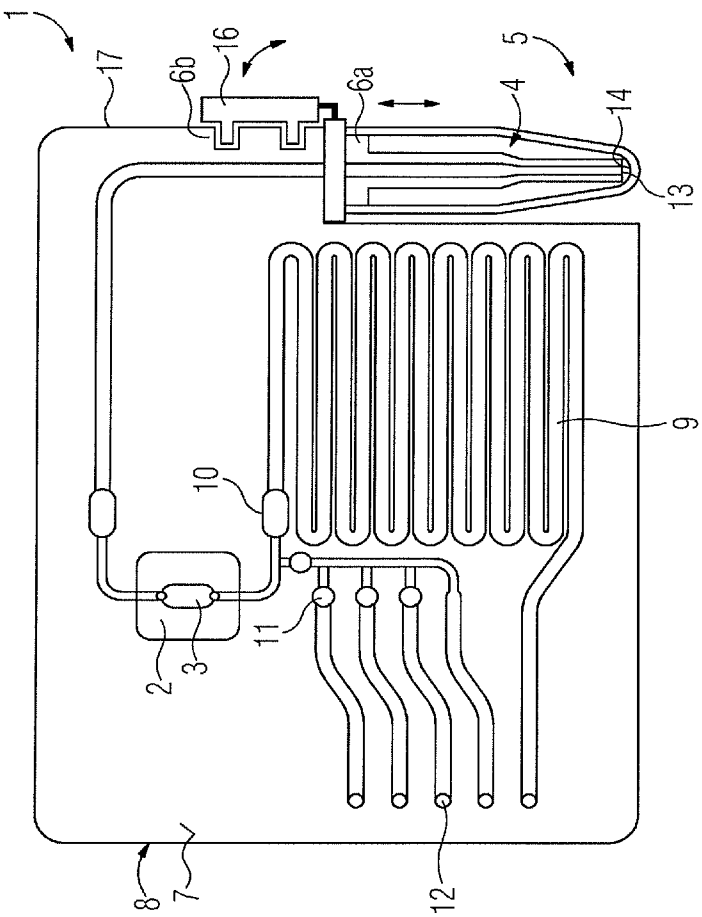
FIG. 2 is a schematic plan view analogous to the one shown in FIG. 1 with a clamping device according to a second exemplary embodiment, with clamping of an E-cup and clamping of a cover of the E-cup.

FIG. 2 shows an exemplary embodiment of the flat body 1 with a clamping device 6*a* and a clamping device 6*b*. The clamping device 6*a* is analogous to the above-described clamping device 6*a*. Additionally, a clamping device 6*b* for clamping a cover of an E-cup 5 has been formed in the flat body 1. The clamping device 6*b* is made of two cutouts in an edge 17 of the flat body 1, adjacent to the second microfluidic device 4. In terms of their dimensions, the recesses have the inverse shape and dimensions of the lower cover part, which points in the direction of the E-cup 5 if the E-cup 5 is folded shut.

The clamping device 6*b* leads to an improved mechanical connection between an E-cup 5 and the flat body 1, and to an increased stability of an arrangement of E-cup 5 and flat body 1. This allows simple handling of flat body 1 in conjunction with an E-cup 5. The second microfluidic device 4 allows liquid interchange between flat body 1 and E-cup 5, particularly if external pumps are connected, via the inlet and outlet openings 12 of the flat body 1. An E-cup 5 can, in conjunction with the flat body 1, serve as a sample vessel for supplying the liquids to be detected or involved in the reaction; it can serve as external reaction vessel or as waste container for liquids to be disposed of.

If use is made of an E-cup 5 with a possible liquid volume of 500 µl, the overall length of the E-cup 5 is 30 mm and the length in the interior of the E-cup 5 is 29 mm. The external diameter of the E-cup 5 is 7.6 mm. However, the external diameter of 10 mm and the internal diameter of 6.5 mm of the circular upper edge of the E-cup 5, which has the form of a flange, are decisive for the dimensions of the clamping device 6*a*. Hence, in this exemplary embodiment, the clamping device 6*a* likewise has a width in the region of 6.5 mm or it is slightly larger, e.g. 6.6 mm. As a result, a mechanical attachment by clamping is achieved when the E-cup 5 is pushed on. The distance of the transition of the clamping device 6*a* to the remainder of the flat body 1 in relation to the tip 13 of the clamping device 6*a* is 29 mm or slightly less at a length of the interior of the E-cup 5. This ensures that when the E-cup is pushed on up to the stop at the transition of the clamping device 6*a* to the remainder of the flat body 1, the tip 13 is arranged in the region of the base 14 of the E-cup 5. As a result, the entire liquid in an E-cup 5 can be handled by the second microfluidic device 4. If the E-cup 5 is not completely plugged onto the clamping device 6*a*, the length of the distance of the transition of the clamping device 6*a* to the remainder of the flat body 1 in relation to the tip 13 of the clamping device 6*a* can also have a longer configuration than 29 mm. In the case where it is unnecessary to use or handle the entire liquid volume in the E-cup 5, the length can also be shorter than 29 mm.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV*, 358 F3d 870, 69 USPQ2d 1865 (Fed. Cir. 2004).

The invention claimed is:

1. A flat body formed as a chip card for biochemical analysis of substances, comprising:

at least two microfluidic devices, including at least one first microfluidic device and a second microfluidic device, said second microfluidic device being a pipette that has been integrally formed in said flat body, wherein said pipette is made from the same material as the flat body and has the same flat thickness as the flat body;

at least one sensor chip integrated in the flat body and in direct contact with the at least one first microfluidic device; and wherein the pipette is located within the confines of a recess formed in the flat body, wherein said recess is large enough for a reaction vessel to be mounted over the pipette with the reaction vessel located substantially completely within said recess, wherein the pipette is in fluidic contact with the sensor chip via the first microfluidic device;

wherein the microfluidic devices are formed on a planar front side of the flat body;

wherein a self-adhesive plastic film completely covers the planar front side of the flat body; and wherein the at least one sensor chip is embedded in a depression in a planar rear side of the flat body.

2. The flat body as claimed in claim 1, wherein the flat body further comprises a first clamping device to attach said reaction vessel onto the flat body surrounding said pipette in a direct mechanical manner.

3. The flat body as claimed in claim 2, wherein the flat body comprises a second clamping device to attach a cover of said reaction vessel onto the flat body in a direct mechanical manner.

4. The flat body as claimed in claim 3, wherein the second microfluidic device has an elongate design and at one end has a tip with a fluidic opening, such that when said E-cup is attached to the first and/or second clamping device, the tip of the second microfluidic device is arranged with the fluidic opening in a region of a lower end of the reaction vessel.

5. The flat body as claimed in claim 4, wherein the flat body is formed of an injection-molded plastic, and.

6. The flat body as claimed in claim 5, wherein the sensor chip has at least one of electric contacts coplanar with the planar rear side, and a sensor array in direct contact with at least one chamber on the planar rear side of the flat body, and wherein the at least two microfluidic devices comprise at least one of channels and/or chambers formed as depressions in the planar rear side of the flat body, valves formed in the flat body, and a recess forming the depression in the planar rear side.

7. The flat body as claimed in claim 6, wherein the flat body has a thickness of substantially one millimeter, a length of substantially 85 millimeters, and a width of substantially 54 millimeters.

8. The flat body as claimed in claim 6, wherein at least one of the microfluidic devices is designed to contain dry reagents, in the channels and/or in reaction chambers, having a cross section of at least one square millimeter.

9. The flat body as claimed in claim 8, wherein the second microfluidic device has a cross section perpendicular to the front side of the flat body with a substantially rectangular outer perimeter and an open recess toward the front side of the flat body.

10. The flat body as claimed in claim 9, wherein the second microfluidic device has a length of substantially 45 millimeters.

11. The flat body as claimed in claim 6, wherein the sensor chip comprises sensors, and wherein the second microfluidic device is in fluidic contact with the sensors of the sensor chip via the at least one first microfluidic device.

12. The flat body as claimed in claim 6, wherein the sensor chip comprises at least one of an array of electrochemical sensors, an integrated circuit for processing electric signals from the sensors, and electric contacts for electric readout of the sensor chip by an external data processing unit.

13. The flat body as claimed in claim 6, wherein the flat body has at least one opening on at least one of the front and rear sides, in fluidic contact with the at least one first microfluidic device and/or connectable to an exterior pump.

* * * * *